United States Patent
Wang et al.

(10) Patent No.: US 11,751,844 B2
(45) Date of Patent: Sep. 12, 2023

(54) ULTRASONIC IMAGING SYSTEM AND METHOD

(71) Applicant: GE Precision Healthcare LLC, Wauwatosa, WI (US)

(72) Inventors: Xin Wang, Wuxi (CN); Hongfei Cai, Wuxi (CN); Kejian Shi, Wuxi (CN); Bing Li, Wuxi (CN); Yanli Chen, Wuxi (CN); Chao Yan, Wuxi (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 51 days.

(21) Appl. No.: 17/343,245

(22) Filed: Jun. 9, 2021

(65) Prior Publication Data
US 2021/0401402 A1 Dec. 30, 2021

(30) Foreign Application Priority Data

Jun. 24, 2020 (CN) .......................... 202010587226.1

(51) Int. Cl.
*A61B 8/00* (2006.01)

(52) U.S. Cl.
CPC ............ *A61B 8/4218* (2013.01); *A61B 8/463* (2013.01); *A61B 8/469* (2013.01); *A61B 8/54* (2013.01)

(58) Field of Classification Search
None
See application file for complete search history.

(56) References Cited

U.S. PATENT DOCUMENTS

| 8,753,278 B2 | 6/2014 | Stoll | |
|---|---|---|---|
| 2003/0167004 A1 | 9/2003 | Dines | |
| 2008/0021317 A1* | 1/2008 | Sumanaweera | A61B 8/4281 600/437 |
| 2009/0088639 A1* | 4/2009 | Maschke | B25J 11/00 600/443 |
| 2010/0204578 A1* | 8/2010 | Schmidt | A61B 90/50 600/443 |
| 2012/0083692 A1* | 4/2012 | Stoll | A61B 8/429 600/437 |
| 2014/0066769 A1* | 3/2014 | Wang | A61B 8/4455 600/443 |

(Continued)

FOREIGN PATENT DOCUMENTS

| CN | 203802492 U | 9/2014 |
|---|---|---|
| CN | 109316207 A | 2/2019 |

*Primary Examiner* — Joel Lamprecht
*Assistant Examiner* — Ashish S Jasani

(57) ABSTRACT

The present invention relates to an ultrasonic imaging system and a respective method. The ultrasonic imaging system includes a scanning assembly including an ultrasonic transducer, an adjustable arm, one end of the adjustable arm connected to the scanning assembly, and a counterweight, connected to the other end of the adjustable arm by means of a cable. The ultrasonic imaging system includes a transmission assembly comprising a drive unit and a transmission unit, the drive unit being capable of acting on the counterweight by means of the transmission unit so as to adjust a pressure applied by the scanning assembly to the tissue to be scanned and a control unit, sending a drive signal to the drive unit, and acquiring, on the basis of the drive signal, the pressure applied by the scanning assembly to the tissue to be scanned.

12 Claims, 7 Drawing Sheets

(56) References Cited

U.S. PATENT DOCUMENTS

| | | | |
|---|---|---|---|
| 2015/0094587 A1* | 4/2015 | Chen | A61B 8/0825 |
| | | | 600/447 |
| 2015/0094588 A1* | 4/2015 | Summers | A61B 8/0825 |
| | | | 600/445 |
| 2016/0338787 A1* | 11/2016 | Popovic | A61B 1/0052 |
| 2017/0188992 A1* | 7/2017 | O'Brien | A61B 8/488 |
| 2018/0055479 A1* | 3/2018 | Lalena | A61B 8/4461 |
| 2018/0256130 A1* | 9/2018 | Wang | A61B 8/4209 |
| 2019/0076115 A1* | 3/2019 | Bax | F16M 11/2078 |

\* cited by examiner

ULTRASONIC IMAGING SYSTEM AND METHOD

FIELD OF THE INVENTION

The present invention relates to the field of medical imaging, and in particular, to an ultrasonic imaging system and an ultrasonic imaging method using the system.

BACKGROUND

Ultrasonic imaging is important means for imaging the interior of the body of a person to be scanned. Generally, ultrasonic imaging systems use several ultrasonic transducer elements to convert electrical energy into ultrasonic pulses. The ultrasonic pulses are sent to the interior of the body of the person to be scanned, and echo signals are generated. The echo signals are received by transducer elements, and are then converted to electrical signals. The electrical signals are processed by a specialized processing device to form a desired ultrasonic image.

Ultrasonic imaging devices have important applications in scanning of many body organs. For example, a full-field breast ultrasonic scanning device may be used to image breast tissue in one or a plurality of planes. During full-field breast ultrasonic scanning, it is usually necessary for a scanning assembly to apply a certain pressure to a tissue to be scanned (e.g., a breast) so as to press the tissue to be scanned and for imaging. Control and adjustment of the pressure described above are important for scanning imaging. On the one hand, an overly low or an overly high pressure would affect ultrasonic image quality; on the other hand, an overly high pressure is likely to pose a safety hazard to the person to be scanned. Disposing a pressure sensor on the scanning assembly to implement pressure measurement has some drawbacks. On the one hand, scanning assemblys generally have a plurality of narrower bezels on which pressure sensors are difficult to secure. On the other hand, measurement of an average pressure applied by the scanning assembly to the tissue to be scanned requires multiple pressure sensors to operate simultaneously, and then the average pressure is further calculated. This increases the complexity of the pressure measurement and costs of the device.

SUMMARY

Provided in some embodiments of the present invention is an ultrasonic imaging system, comprising: a scanning assembly, comprising an ultrasonic transducer, and configured to perform ultrasonic imaging on a tissue to be scanned; an adjustable arm, one end of the adjustable arm connected to the scanning assembly; a counterweight, connected to the other end of the adjustable arm by means of a cable; a transmission assembly, comprising a drive unit and a transmission unit, the drive unit being capable of acting on the counterweight by means of the transmission unit so as to adjust a pressure applied by the scanning assembly to the tissue to be scanned; and a control unit, sending a drive signal to the drive unit, and acquiring, on the basis of the drive signal, the pressure applied by the scanning assembly to the tissue to be scanned.

Further provided in some other embodiments of the present invention is a method of performing ultrasonic imaging by using the aforementioned ultrasonic imaging system, comprising: adjusting a position of the imaging assembly, so that the imaging assembly is close to a surface of a tissue to be imaged; sending a drive signal to the drive unit by using the control unit, and controlling the drive unit to act on the counterweight so as to adjust a pressure applied by the scanning assembly to the tissue to be scanned; acquiring, on the basis of the drive signal, the pressure applied by the scanning assembly to the tissue to be scanned; and performing ultrasonic imaging by using the scanning assembly.

BRIEF DESCRIPTION OF THE DRAWINGS

The present invention will be better understood by reading the following description of non-limiting embodiments with reference to the accompanying drawings, where.

DETAILED DESCRIPTION

Specific implementations of the present invention will be described in the following. It should be noted that during the specific description of the implementations, it is impossible to describe all features of the actual implementations in detail in present invention for the sake of brief description. It should be understood that in the actual implementation of any of the implementations, as in the process of any engineering project or design project, a variety of specific decisions are often made in order to achieve the developer's specific objectives and meet system-related or business-related restrictions, which will vary from one implementation to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. "First," "second" and similar words used in the present invention and the claims do not denote any order, quantity or importance, but are merely intended to distinguish between different constituents. "One," "a(n)" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

Although some embodiments of the present invention are presented in the particular context of human breast ultrasound, it should be understood that the present invention is applicable to ultrasound scanning of any externally accessible human or animal body part (for example, abdomen, legs, feet, arms, or neck), and is also applicable to other medical imaging devices (for example, X-ray scanning) with a similar mechanical structure.

Figure 1:
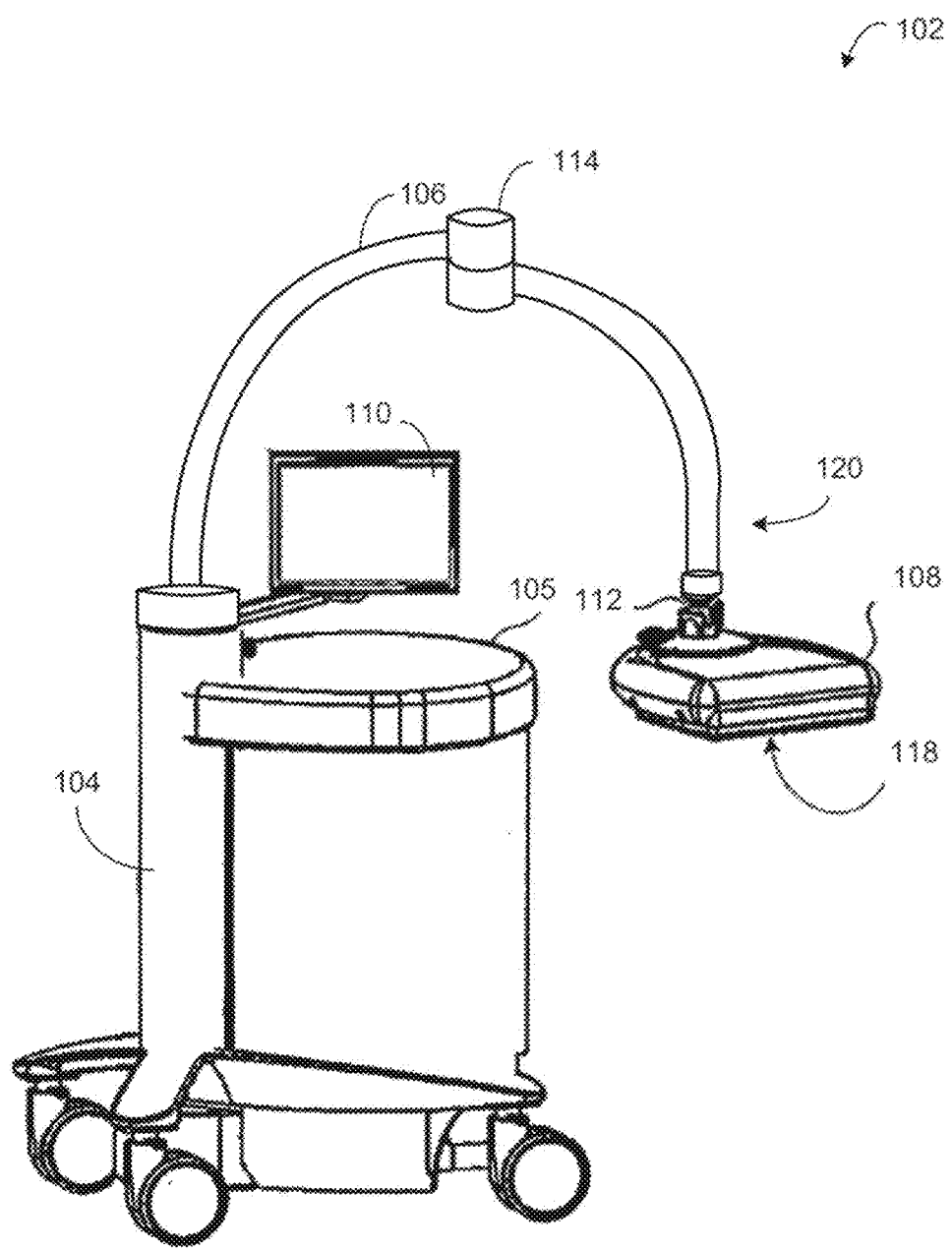
FIG. 1 is a perspective view of an ultrasonic imaging system according to an embodiment of the present invention.

FIG. 1 shows a perspective view of a full-field breast ultrasound (FFBU) imaging system 102 (hereinafter also generally referred to as an ultrasonic imaging system 102) according to an embodiment. The ultrasonic imaging system 102 includes a frame 104, an ultrasonic processor housing 105 comprising an ultrasonic processor, a movable and adjustable support arm (for example, an adjustable arm) 106 including a hinge joint 114, a scanning assembly 108 connected to a first end 120 of the adjustable arm 106 by means of a ball and socket connector (for example, a ball joint) 112, and a display 110 connected to the frame 104. The display 110 is connected to the frame 104 at a joining point where the adjustable arm 106 enters the frame 104. Since the display 110 is directly connected to the frame 104 rather than the adjustable arm 106, the display 110 does not affect the weight of the adjustable arm 106 and the balancing mechanism of the adjustable arm 106. In one example, the display 110 may rotate in horizontal and transverse directions (for example, rotatable about a central axis of the frame 104), but cannot move vertically. In an alternative example, the display 110 may also be vertically movable. Although FIG. 1 illustrates the display 110 connected to the frame 104, in other examples, the display 110 may be connected to different parts of the ultrasonic imaging system 102, such as, connected to the ultrasonic processor housing 105, or positioned away from the ultrasonic imaging system 102.

In an embodiment, the adjustable arm 106 is configured and adapted so that the scanning assembly 108 is neutrally buoyant in space, or has a light net downward weight (for example, 1-2 kg) for pressing the breast, while allowing easy user operation. In an alternative embodiment, the adjustable arm 106 is configured so that the scanning assembly 108 is neutrally buoyant in space during positioning of a scanner on a tissue of a patient. Then, after the scanning assembly 108 is positioned, internal parts of the ultrasonic imaging system 102 may be adjusted to apply a desired downward weight for pressing the breast and improved image quality. In one example, the downward weight (for example, a force) may be in a range of 2-11 kg. The internal parts described above may generally be disposed within the frame 104, and examples of the internal parts will be discussed in detail below.

As described above, the adjustable arm 106 includes the hinge joint 114. The hinge joint 114 divides the adjustable arm 106 into a first arm portion and a second arm portion. The first arm portion is connected to the scanning assembly 108, and the second arm portion is connected to the frame 104. The hinge joint 114 allows the second arm portion to rotate relative to the second arm portion and the frame 104. For example, the hinge joint 114 allows the scanning assembly 108 to translate transversely and horizontally, but not vertically, relative to the second arm portion and the frame 104. In such manner, the scanning assembly 108 may rotate towards the frame 104 or away from the frame 104. However, the hinge joint 114 is configured to allow the entire adjustable arm 106 (for example, the first arm portion and the second arm portion) to move vertically together as a whole (for example, translating upwards and downwards along with the frame 104).

The scanning assembly 108 may include a film 118 that is in a substantially tensioned state to be at least partially attached, for pressing the breast. The film 118 has a bottom surface for contacting the breast, and when the bottom surface is in contact with the breast, the transducer sweeps over a top surface of the film to scan the breast. In one example, the film is a tensioned fabric sheet.

A fully functional ultrasonic engine may be provided within the ultrasonic processor housing 105, and is configured to drive the ultrasonic transducer, and generate volumetric breast ultrasound data from a scan in conjunction with related position and orientation information. In some examples, volumetric scan data may be transmitted to another computer system by using any of a variety of data transmission methods known in the art so as to be further processed, or the volumetric scan data may be processed by the ultrasonic engine. A general-purpose computer/processor integrated with the ultrasonic engine may further be provided for general user interface and system control. The general-purpose computer may be a self-contained stand-alone unit, or may be remotely controlled, configured, and/or monitored by remote stations connected across networks.

Figure 2:
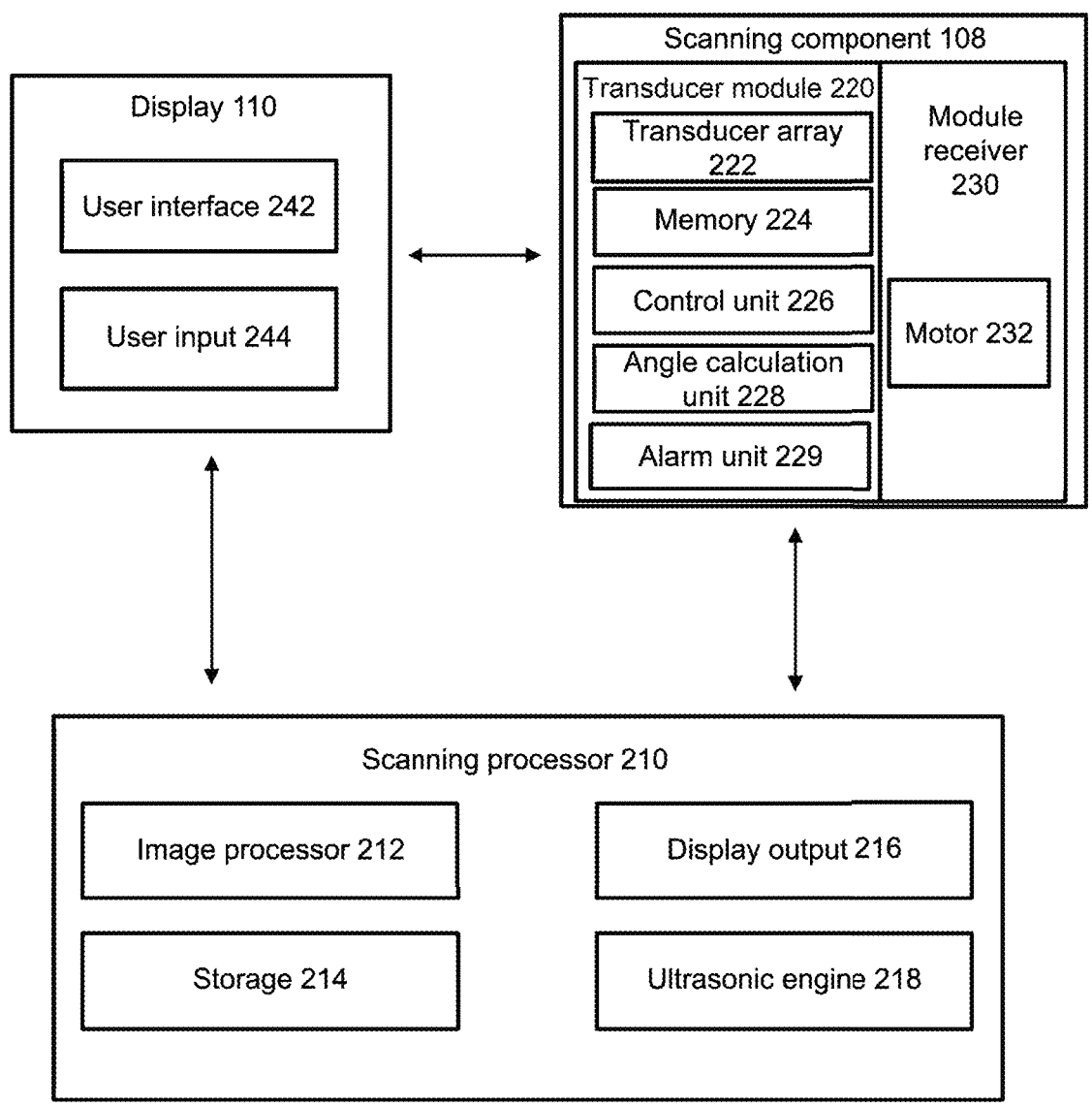
FIG. 2 is a schematic block diagram of various system parts according to an embodiment of the present invention.

FIG. 2 is a block diagram 200 that schematically illustrates various system parts of the ultrasonic imaging system 102, including the scanning assembly 108, the display 110, and a scanning processor 210. In one example, the scanning processor 210 may be included within the ultrasonic processor housing 105 of the ultrasonic imaging system 102. As shown in the embodiment of FIG. 2, the scanning assembly 108, the display 110, and the scanning processor 210 are independent parts communicating with each other; however, in some embodiments, one or more of these components may be integrated (for example, the display and the scanning processor may be included in a single part).

Reference is first made to the scanning assembly 108, and the scanning assembly includes a transducer module 220 connected to a module receiver 230. The module receiver 230 may be positioned within a housing (e.g., attached to an arm 106 of a scanning device), and the housing is configured to remain stationary during scanning, while the module receiver 230 is configured to translate relative to the housing during scanning. In order to translate automatically relative to the housing during scanning, the module receiver includes a motor 232 activated by the scanning processor 210, see detailed description below.

The transducer module 220 includes a transducer array 222 of transducer elements, such as piezoelectric elements, which converts electrical energy into ultrasonic waves, and then detects reflected ultrasonic waves. The transducer module 220 is configured to be removably connected to the module receiver 230 by means of a connector. The connector may include complementary connectors on the transducer module and the module receiver (for example, a first connector on the transducer module is configured to be connected to a second connector on the module receiver), in order to establish a mechanical connection and an electrical connection between the module receiver and the transducer module.

The transducer module 220 may further include a memory 224. The memory 224 may be a non-transitory memory, and is configured to store various parameters of the transducer module 220, such as transducer usage data (e.g., a count of scans performed, a total amount of time spent during scanning, etc.), as well as specification data of the transducer (e.g., the number of elements of the transducer array, array geometry, etc.) and/or identification information of the transducer module 220, such as a serial number of the transducer module. The memory 224 may include movable and/or permanent devices, and may include an optical memory, a semiconductor memory, and/or a magnetic memory, etc. The memory 224 may include a volatile, non-volatile, dynamic, static, read/write, read only, random access, sequential access, and/or additional memory. In an example, the memory 224 may include a RAM. Additionally or alternatively, the memory 224 may include an EEPROM.

The memory 224 may store non-transitory instructions executable by a controller or processor (such as a control unit 226) so as to perform one or more methods or routines as described below. The control unit 226 may receive output of a deflection angle of the scanning assembly 108 acquired from an angle calculation unit 228 of the transducer module 220. Furthermore, in some embodiments, the motor 232 may be activated via a signal from the control unit 226 so as to initiate a scan. However, in other embodiments, the motor 232 may be activated via a signal from the separate scanning processor 210.

For example, the scanning assembly 108 may communicate with the scanning processor 210 so as to send raw scan data to an image processor. Furthermore, in some examples, data stored in the memory 224 and/or output from the sensor 228 may be sent to the scanning processor 210. Further, various activities of the scanning assembly 108 (e.g., translation of the module receiver 230 and activation of the transducer elements) may be initiated in response to signals from the scanning processor 210. For example, the scanning assembly 108 may optionally communicate with the display 110 so as to indicate a user to reposition the scanning assembly as described above, or to receive information from the user (via user input 224).

Turning now to the scanning processor 210, the scanning processor includes an image processor 212, a storage 214, display output 216, and an ultrasonic engine 218. The ultrasonic engine 218 may drive activation of the transducer elements of the transducer array 222 of the transducer module 220, and in some embodiments, the motor 232 may be activated. Furthermore, the ultrasonic engine 218 may receive raw image data (e.g., ultrasonic echoes) from the scanning assembly 108. The raw image data may be sent to the image processor 212 and/or a remote processor (e.g., via a network), and processed to form a displayable image of a tissue sample. It should be understood that in some embodiments, the image processor 212 may be included in the ultrasonic engine 218.

Information may be transmitted from the ultrasonic engine 218 and/or the image processor 212 to a user of the ultrasonic imaging system 102 via the display output 216 of the scanning processor 210. In an example, the user of the scanning device may include an ultrasonic technician, a nurse, or a physician such as a radiologist. For example, a processed image of scanned tissue may be sent to the display 110 via the display output 216. In another example, information related to parameters of the scan (such as progress of the scan) may be sent to the display 110 via the display output 216. The display 110 may include a user interface 242 configured to display images or other information to the user. Furthermore, the user interface 242 may be configured to receive input from the user (such as by means of the user input 244), and send the input to the scanning processor 210. In one example, the user input 244 may be a touch screen of the display 110. However, other types of user input mechanisms are also possible, such as a mouse, a keyboard, and the like.

The scanning processor 210 may further include the storage 214. Similar to the memory 224, the storage 214 may include movable and/or permanent devices, and may include an optical memory, a semiconductor memory, and/or a magnetic memory, etc. The storage 214 may include a volatile, non-volatile, dynamic, static, read/write, read only, random access, sequential access, and/or additional memory. The storage 214 may store non-transitory instructions executable by a controller or processor (such as the controller 218 or the image processor 212) so as to perform one or more methods or routines as described below. The storage 214 may store raw image data received from the scanning assembly 108, processed image data received from the image processor 212 or the remote processor, and/or additional information.

Figure 3:
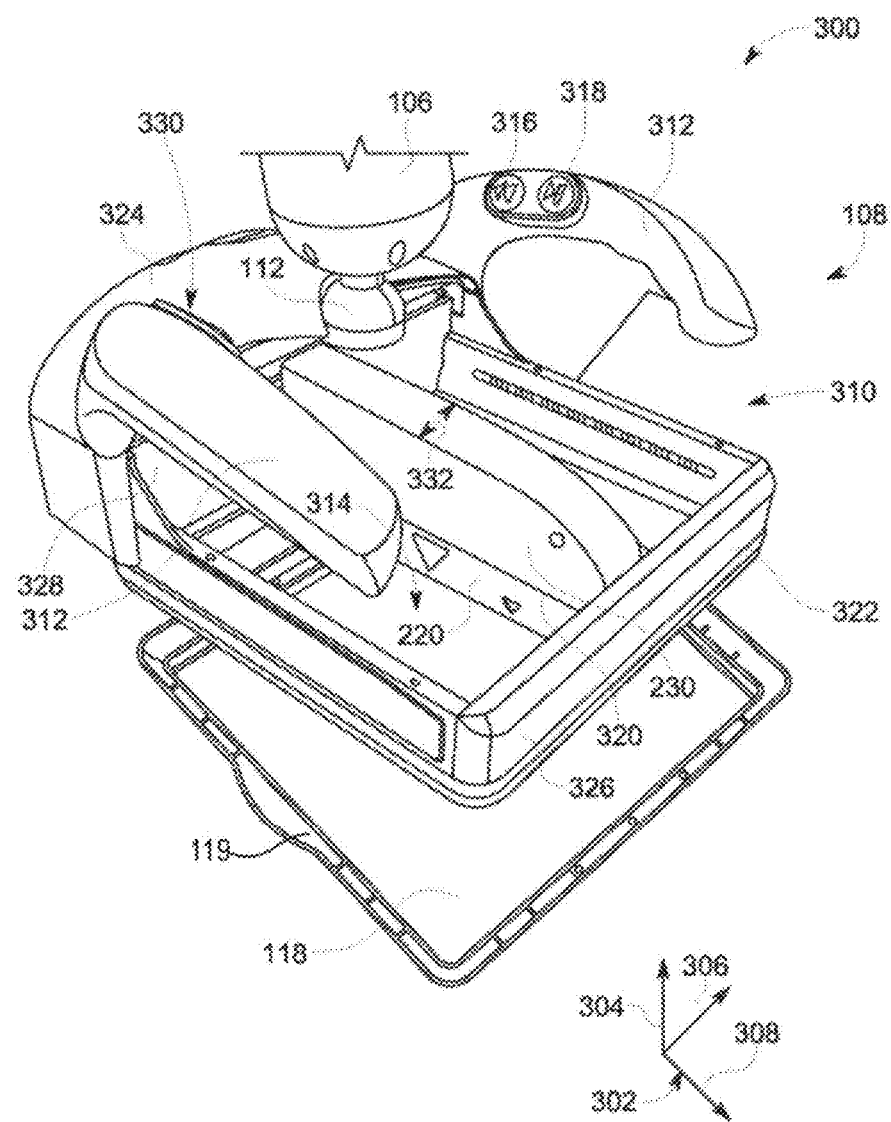
FIG. 3 is a perspective view of a scanning assembly according to an embodiment of the present invention.

FIG. 3 shows a schematic diagram 300 of an isometric view of the scanning assembly 108 connected to the adjustable arm 106. The schematic diagram 300 includes a coordinate system 302, and the coordinate system 302 includes a vertical axis 304, a horizontal axis 306, and an abscissa axis 308.

The scanning assembly 108 includes a housing 310, the transducer module 220, and the module receiver 230. The housing 310 includes a frame 322 and a handle portion 324, and the handle portion includes two handles 312. The two handles 312 oppose each other across a transverse axis of the scanning assembly 108, and the transverse axis is centered on the adjustable arm 106 and defined relative to the transverse axis 308. The frame 322 is rectangular, and an inner periphery of the frame 322 defines an opening 314. The opening 314 provides space (e.g., a void volume), for translating the module receiver 230 and the transducer module 220 during a scanning process. In another example, the frame 322 can have another shape, such as a square having the square opening 314. Additionally, the frame 322 has a thickness defined between the inner periphery and an outer periphery of the frame 322.

The frame 322 includes four sets of side walls (e.g., a set including inner and outer side walls, the inner side walls defining the opening 314). In particular, the frame 322 includes a front side wall 326 and a rear side wall 328, the rear side wall 328 is directly connected to the handle portion 324 of the housing 310, and the front side wall 326 is opposite to the rear side wall 328 with respect to the horizontal axis 306. The frame 322 further includes right and left side walls, the corresponding side walls opposing each other and both being in a plane defined by the vertical axis 304 and the transverse axis 308.

The frame 322 of the housing 310 further includes a top side and a bottom side, and the top side and the bottom side are defined relative to the vertical axis 304. The top side faces the adjustable arm 106. The film 118 is disposed across the opening 314. More specifically, the film 118 is connected to the bottom side of the frame 322. In an example, the film 118 is a diaphragm that remains tensioned across the opening 314. The film 118 may be made from a flexible but non-stretchable material, and the material is thin, waterproof, durable, highly acoustically transparent, resistant to chemical corrosion, and/or biocompatible. As described above, the bottom surface of the film 118 may contact a tissue (e.g., a breast) during scanning, and an upper surface of the film 118 may at least partially contact the transducer module 220 during scanning. As shown in FIG. 3, the film 118 is permanently connected to a hard-housing holding portion 119 surrounding the periphery of the film 118. The holding portion 119 is connected to the bottom side of the frame 322. In one example, the holding portion 119 can be fastened to a lip-like edge on the bottom side of the frame 322 of the housing 310, so that the film 118 does not become unconnected during scanning, but is still removably connected to the frame 322. As discussed further herein with respect to FIGS. 4-9, the film 118 may not be permanently connected to the hard-housing holding portion 119, and thus the film 118 may not be connected to the frame 322 by means of the hard-housing holding portion 119. Instead, the film 118 may be directly and removably connected to the frame 322.

The handle portion 324 of the housing 310 includes the two handles 312 for moving the scanning assembly 108 in space and positioning the scanning assembly 108 on a tissue (e.g., on a patient). In an alternative embodiment, the housing 310 may not include the handle 312. In an example, the handle 312 may be integrally formed with the frame 322 of the housing 310. In another example, the handle 312 and the frame 322 may be formed separately and then mechanically connected together to form the entire housing 310 of the scanning assembly 108.

As shown in FIG. 3, the scanning assembly 108 is connected to the adjustable arm 106 by means of the ball joint 112 (e.g., a ball and socket connector). Specifically, a top dome portion of the handle portion 324 is connected to the ball joint 112. The top of the handle portion 324 includes a depression forming a socket, and a ball of the ball joint 112 is fit in the socket. The ball joint 112 is movable in multiple directions. For example, the ball joint 112 provides rotational motion of the scanning assembly relative to the adjustable arm 106. The ball joint 112 includes a locking mechanism for locking the ball joint 112 in place, thereby holding the scanning assembly 108 stationary relative to the adjustable arm 106. Furthermore, the ball joint 112 may also be configured to only rotate but not to move in multiple directions, such as oscillating.

Additionally, as shown in FIG. 3, the handle 312 of the handle portion 324 includes buttons for controlling scanning and adjusting the scanning assembly 108. Specifically, a first handle of the handles 312 includes a first weight adjustment button 316 and a second weight adjustment button 318. The first weight adjustment button 316 may reduce a load applied to the scanning assembly 108 from the adjustable arm 106. The second weight adjustment button 318 may increase a load applied to the scanning assembly 108 from the adjustable arm 106. Increasing the load applied to the scanning assembly 108 may increase the pressure and the amount of pressing applied to the tissue on which the scanning assembly 108 is placed. Furthermore, increasing the load applied to the scanning assembly increases the effective weight of the scanning assembly on the tissue to be scanned. In one example, increasing the load may press a tissue of a patient, such as a breast. In such way, varying amounts of pressure (e.g., load) may be applied consistently with the scanning assembly 108 during scanning in order to obtain high quality images by using the transducer module 220.

Prior to the scanning process, a user (e.g., an ultrasonic technician or physician) may position the scanning assembly 108 on a patient or a tissue. Once the scanning assembly 108 is properly positioned, the user may adjust a weight (e.g., adjusting an amount of pressing) of the scanning assembly 108 on the patient by using the first weight adjustment button 316 and/or the second weight adjustment button 318. Then, the user may initiate the scanning process by means of additional control on the handle portion 324 of the housing 310. For example, as shown in FIG. 3, the second handle of the handles 312 includes two additional buttons 330 (not separately shown). The two additional buttons 330 may include a first button for initiating a scan (e.g., once the scanning assembly has been placed on the tissue/patient and an amount of pressing has been selected) and a second button for stopping the scan. In one example, once the first button is selected, the ball joint 112 may be locked, thereby stopping transverse and horizontal movement of the scanning assembly 108.

The module receiver 230 is positioned within the housing 310. Specifically, the module receiver 230 is mechanically connected to a first end of the housing 310 at a rear side wall 328 of the frame 322, and the first end is closer to the adjustable arm 106 than a second end of the housing 310. The second end of the housing 310 is located at a front side wall 326 of the frame 322. In one example, the module receiver 230 is connected to the first end by means of a protruding portion of the module receiver 230, and the protruding portion is connected to the motor 230. The protruding portion is connected to the motor of the module receiver 230 (e.g., the motor 232 described with reference to FIG. 2 above).

As described above, the housing 310 is configured to remain stationary during scanning. In other words, once the weight applied to the scanning assembly 108 is adjusted by means of the adjustable arm 106 and then the ball joint 112 is locked, the housing 310 may remain in the resting position without translating in the horizontal or transverse direction. However, the housing 310 may still translate vertically as the adjustable arm 106 move vertically.

Instead, the module receiver 230 is configured to translate relative to the housing 310 during scanning. As shown in FIG. 3, the module receiver 230 translates horizontally along a horizontal axis 306 relative to the housing 310. The motor of the module receiver 230 may slide the module receiver 230 along an upper surface of the first end of the housing 310.

The transducer module 220 is removably connected to the module receiver 230. Therefore, during scanning, the transducer module 220 and the module receiver 230 translate horizontally. During scanning, the transducer module 220 sweeps horizontally across the breast under the control of the motor of the module receiver 230, and meanwhile, a contact surface of the transducer module 220 contacts the film 118. The transducer module 220 and the module receiver 230 are connected together at a module interface 320. The module receiver 230 has a width 332 that is the same as a width of the transducer module 220. In an alternative embodiment, the width 332 of the module receiver may be different from the width of the transducer module 220. In some embodiments, the module interface 320 includes a connector between the transducer module 220 and the module receiver 230, and the connector includes mechanical and electrical connections.

Figure 4:
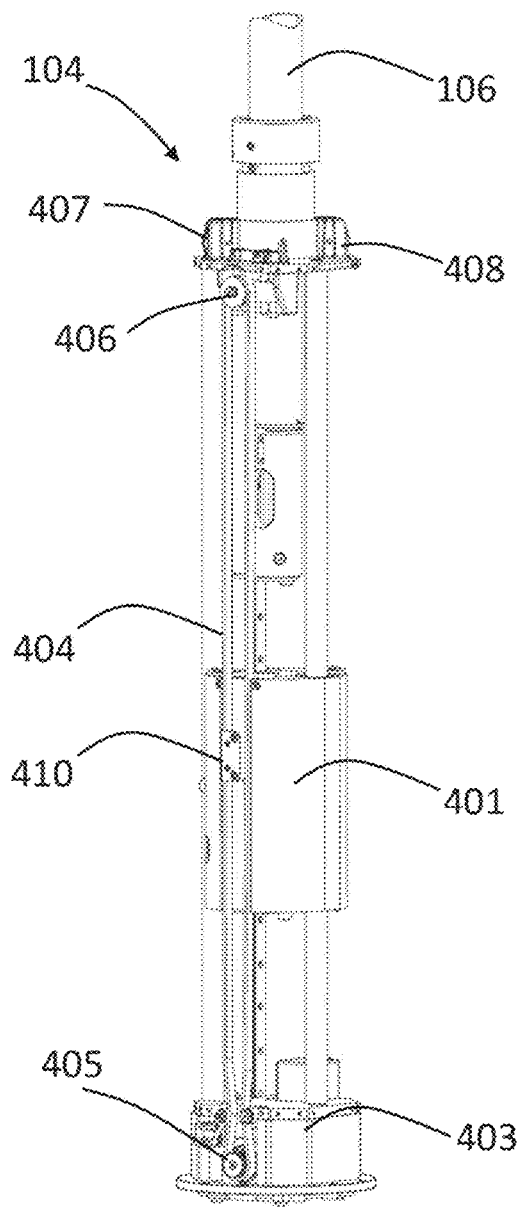
FIG. 4 is a schematic diagram of an internal structure of an ultrasonic imaging system according to an embodiment of the present invention.
Figure 5:
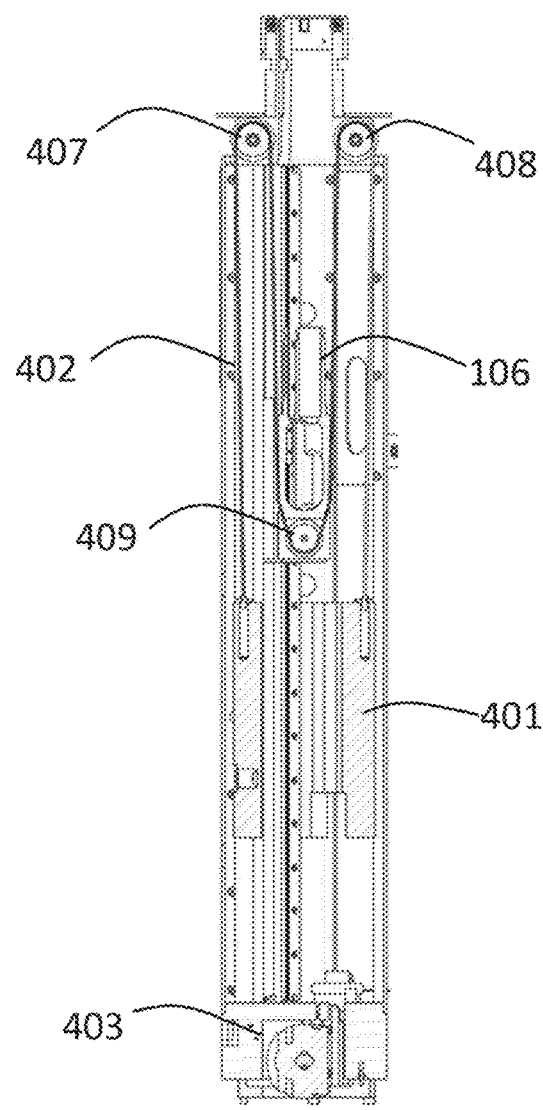
FIG. 5 is a cross-sectional view of an internal structure of an ultrasonic imaging system according to an embodiment of the present invention.

Referring to FIGS. 4 and 5, schematic diagrams of an internal structure of the ultrasonic imaging system 102 according to embodiments of the present invention are shown. Parts specifically for effective weight adjustment of the scanning assembly 108 (not shown in FIGS. 4 and 5) are included inside the frame 104 of the ultrasonic imaging system 102. Specifically, one end of the adjustable arm 106 is connected to the scanning assembly 108 as shown in FIG. 1, and the other end of the adjustable arm 106 is disposed inside the frame 104. The frame 104 can be used for securing the adjustable arm 106 and guidance during up and down movement. A counterweight 401 is further disposed inside the frame 104. The counterweight 401 may be connected to the other end of the adjustable arm 106 by means of a cable 402. The weight of the counterweight 401 may be particularly designed, and the weight thereof may be approximately equal to the sum of the weights of the scanning assembly 108 and the adjustable arm 106. In such manner of configuration, the scanning assembly 108 is neutrally buoyant in space, or has a light net upward or downward weight for pressing the breast, while allowing easy user operation. The cable 402 may be a steel cable. In order to facilitate a sliding connection between the counterweight 401 and the adjustable arm 106, a pulley structure may be disposed in an appropriate position. As shown in FIG. 5, two fixed pulleys, a first fixed pulley 407 and a second fixed pulley 408, may be disposed on top of the frame 104. In addition, a third fixed pulley 409 may be disposed at the bottom of the adjustable arm 106. The cable 402 winds along the aforementioned three fixed pulley structures, and two ends of the cable 402 may be respectively secured to the counterweight 401. In this way, a smooth connection between the counterweight 401 and the adjustable arm can be achieved. As the user presses the adjustable arm 106 downwards, the adjustable arm 106 moves downwards. In this case, the adjustable arm 106 acts on the cable 402 by means of the third fixed pulley 409 at the bottom, and the cable 402 applies an increased upward pulling force to the counterweight 401 to raise the counterweight 401. Conversely, as the user lifts the adjustable arm 106, the adjustable arm 106 moves upwards. In this case, a pressure applied by the third fixed pulley 409 at the bottom of the adjustable arm 106 to the cable 402 decreases. Correspondingly, the pulling force applied by the cable 402 to the counterweight 401 decreases, causing the counterweight 401 to descend. As described above, the weight of the counterweight 401 may be configured to be approximately equal to the sum of the weights of the scanning assembly 108 and the adjustable arm 106. In this way, when the user manually adjusts the positions of the adjustable arm 106 and the scanning assembly 108, due to the presence of the counterweight, it is easy for realizing force balance of the scanning assembly 108 in an arbitrary position, so that the scanning assembly remains in a stable position. It should be noted that the material of the cable 402 may be any material, for example, a steel wire, a polymer, or the like. The cable 402 may be in the shape of a rope, or may be in the shape of a driving belt, or any other shape capable of connecting the counterweight 401 and the adjustable arm 106.

In addition, a transmission assembly may further be disposed to act on the counterweight 401, thereby acting on the bottom of the adjustable arm 106, further adjusting the pressure applied by the scanning assembly 108 to the tissue to be scanned. Referring to FIGS. 4 and 5, in some embodiments, the transmission assembly may include a drive unit 403 and a transmission unit 404. The drive unit 403 acts on the counterweight 401 by means of the transmission unit 404, so as to adjust the pressure from the scanning assembly 108 to the tissue to be scanned. In such manner of configuration, adjusting the pressure of the scanning assembly 108 by electrically controlling the drive unit 403 can be implemented. For example, the user may manually adjust the position of the scanning assembly 108 so that the scanning assembly is close to the surface of the tissue to be scanned. In this case, the pressure applied by the scanning assembly 108 to the tissue to be scanned is still low. Subsequently, the user may activate the drive unit 403 to drive the transmission unit 404 to act on the counterweight 401, thereby performing the aforementioned pressure adjustment. Types of the drive unit 403 and the transmission unit 404 may be various. For example, the drive unit 403 may be a structure including a motor, and the transmission unit 404 may be a driving belt. When the transmission unit 404 is a driving belt, a drive wheel 405 may be disposed on an output shaft of the drive unit 403 to drive the transmission unit 404 to move. A driven wheel 406 may further be disposed at an appropriate position, for example the top, of the frame 104, and be configured to tension and secure the transmission unit 404. One edge of the transmission unit 404 is secured to the counterweight 401 by means of a transmission unit securing device 410. In this way, when the drive unit 403 drives the transmission unit 404 to rotate, the drive unit can act on the counterweight 401. Note that the transmission unit 404 may be other types of structures besides the driving belt structure, for example, a slide rail structure, a rack structure, etc.

In some embodiments, the drive unit 403 may include a motor and a clutch. The motor is connected to the clutch, and the clutch is connected to the transmission unit 404. In such manner of configuration, it is convenient for the user to independently select manual adjustment or electrical adjustment. When the positions of the adjustable arm 106 and the scanning assembly 108 need to be manually adjusted, the user can select (by using a key to select) to configure the motor and the clutch to be in a separate state. In this case, the motor does not act on the counterweight by means of the transmission unit 404, and the user can manually control the positions of the adjustable arm 106 and the scanning assembly 108. When pressure adjustment needs to be performed, the user can select to operate the motor with the clutch. In this case, the motor can transmit driving force to the transmission unit 404 by means of the clutch, so as to act on the counterweight to achieve pressure adjustment.

Figure 6:
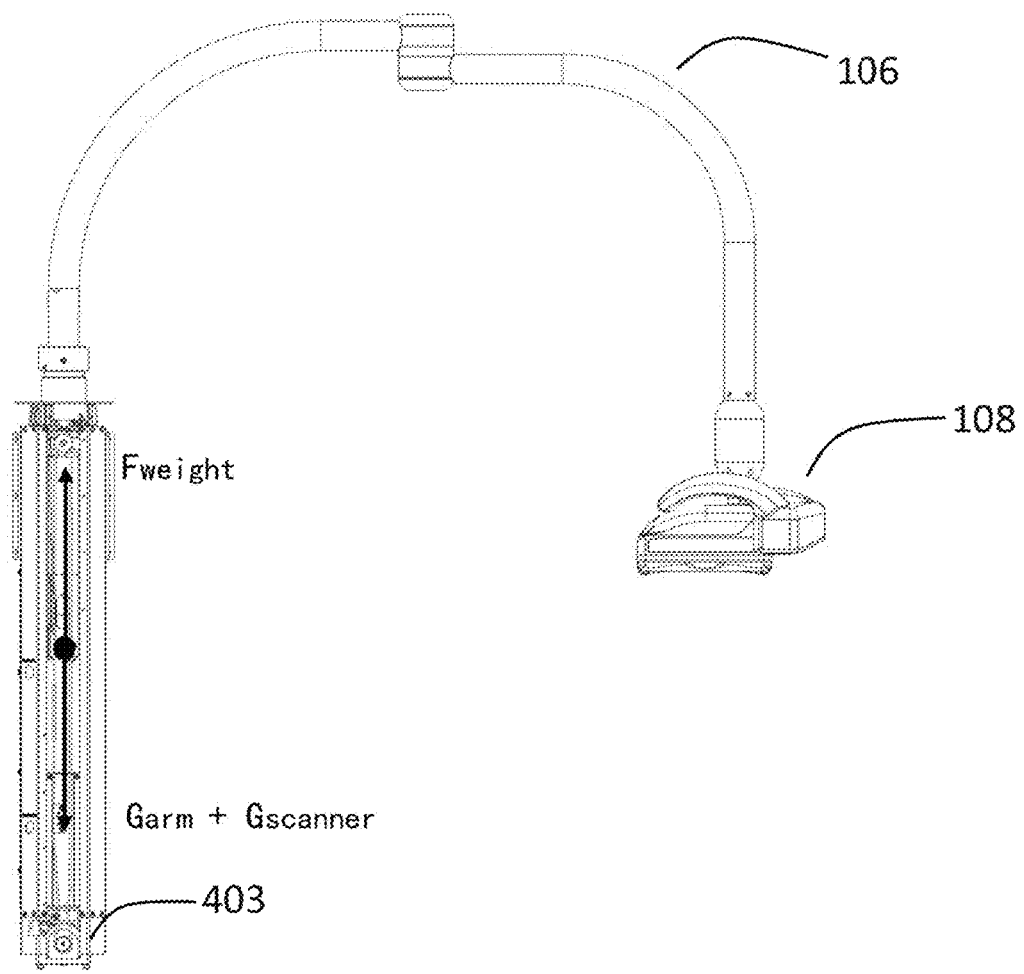
FIG. 6 is a schematic force diagram of an ultrasonic imaging system according to an embodiment of the present invention.

FIG. 6 is a schematic force diagram of an ultrasonic imaging system according to some embodiments of the present invention. From the above description, it can be seen that when the drive unit 403 does not act on the counterweight 401, gravity Gweight of the counterweight 401 substantially all acts on the bottom of the adjustable arm 106, that is, a force Fweight from the counterweight 401 to the bottom of the adjustable arm 106 is numerically equal to Gweight. As described above, Gweight may be configured to be substantially equal to the sum of gravity Garm of the adjustable arm 106 and gravity Gscanner of the scanning assembly 108. In this case, it would be realized that Fweight=Garm+Gscanner, so that the scanning assembly 108 substantially does not act on the tissue to be scanned. When a specific pressure needs to be applied to the tissue to be scanned, the drive unit 403 may be controlled to apply a driving force Fmotor to the counterweight 401. In this case, Fweight is equal to Gweight minus Fmotor, that is, Fweight=Gweight−Fmotor, or Fweight+Fmotor=Gweight. Obviously in this case, Fweight is less than Garm+Gscanner. The scanning assembly 108 is subjected to unbalanced forces due to the decrease in Fweight, resulting in a tendency to press downwards the tissue to be scanned. In this case, the scanning assembly generates a downward pressure Fscanner, and meanwhile is subjected to a reaction force from the tissue to be scanned. As the downward pressure increases, force balance of the scanning assembly 108 is eventually reached again. When balance is eventually reached, Fweight+Fscanner=Garm+Gscanner. From the above description, it can be seen that Fweight+Fmotor=Gweight=Garm+Gscanner, so that Fweight+Fscanner=Fweight+Fmotor. It is understood that, when the balanced state is reached again, Fscanner=Fmotor, that is, the driving force Fmotor applied by the drive unit 403 to the counterweight 401 is numerically equal to the downward pressure Fscanner from the scanning assembly 108. On the basis of this analysis, it is found in the present invention that the pressure from the scanning assembly 108 to the tissue to be scanned can be obtained by measuring the driving force from the drive unit 403 to the counterweight 401.

In some embodiments, the drive unit 403 may include a motor structure. When the user controls the drive unit 403, the control unit 226 in FIG. 2 may be used to send a drive signal to the drive unit 403, and the driving force Fmotor of the drive unit 403 is acquired directly on the basis of the drive signal, so as to acquire the pressure applied by the scanning assembly 108 to the tissue to be scanned.

A variety of methods can be used for the aforementioned acquisition. For example, a storage unit may be disposed, and a correspondence between the aforementioned drive signal and the pressure from the scanning assembly 108 to the tissue to be scanned is stored in the storage unit. The correspondence may be obtained by performing measurement after the imaging system is installed. For example, by giving a certain current value of a drive signal, a corresponding downward pressure of the scanning assembly 108 in this case is measured. Then, by adjusting the current value, different downward pressures are obtained. Then, fitting is performed on the data to obtain a correspondence between the aforementioned drive signal and the pressure from the scanning assembly 108 to the tissue to be scanned. When the control unit needs to acquire the pressure, the control unit can acquire the pressure on the basis of the drive signal and the correspondence stored in the storage unit. The downward pressure may be measured by causing the bottom of the scanning assembly 108 to contact a pressure sensor, or may be measured by connecting a force testing device to the adjustable arm 106. A drive signal-pressure correspondence equation may be acquired by performing fitting on test results, and stored in a storage unit, or the test results may be directly stored in a storage unit, or in any other manner.

Figure 7:
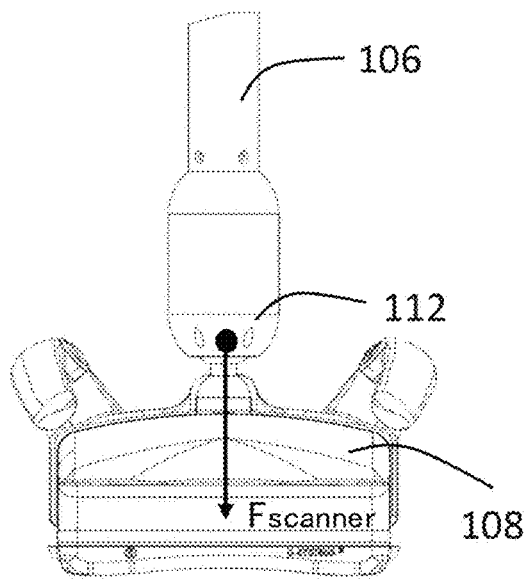
FIG. 7 is a schematic diagram of a scanning assembly according to an embodiment of the present invention.

In some embodiments, the scanning assembly 108 is configured to move in a direction perpendicular to the tissue to be scanned, as shown in FIG. 7. In this case, the downward pressure Fscanner of the scanning assembly 108 is numerically equal to the pressure on the tissue to be scanned.

Figure 8:
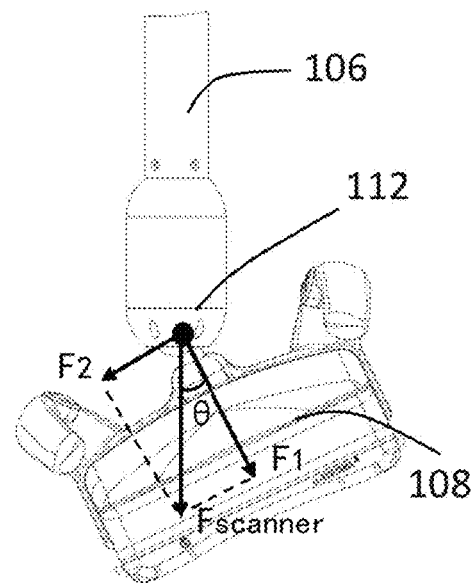
FIG. 8 is a schematic diagram of a scanning assembly according to an embodiment of the present invention.

In some other embodiments, the ball and socket connector 112 is configured to allow moving freely within a certain range of angles. In this case, the pressure from the scanning assembly 108 to the tissue to be scanned and the downward pressure Fscanner form a certain angle $\theta$ (that is, a deflection angle of the scanning assembly 108 relative to an end of the adjustable arm 106), as shown in FIG. 8. In this case, the pressure F1 from the scanning assembly 108 to the tissue to be scanned is equal to a component force of Fscanner in a plane perpendicular to the tissue to be scanned, that is, F1=Fscanner*cos $\theta$. In this case, the aforementioned deflection angle $\theta$ of the scanning assembly 108 relative to an end of the adjustable arm 106 may be calculated by using the angle calculation unit 228 in FIG. 2. On the basis of the aforementioned drive signal in combination with the deflection angle $\theta$, the control unit 226 can acquire the pressure applied by the scanning assembly 108 to the tissue to be scanned. The type of the angle calculation unit 228 may be various, including an angle calculation device such as an accelerometer, a gyroscope, and an inertial measurement unit (IMU). The angle calculation unit 228 may be disposed inside or outside the scanning assembly 108, so as to measure the deflection angle. It should be noted that, the aforementioned configuration of the scanning assembly is not limited. If the scanning assembly 108 is not angularly deflected during scanning, the angle measurement unit 228 is not required. Noted that, although the control unit in FIG. 2 is disposed on the scanning assembly 108, it should be understood that the position of the control unit may be varied. In addition to the position of the control unit 226, the control unit may also be disposed in any position such as in the housing 105 or integrated on the drive unit 403. The control unit may also be integrated within the scanning processor 210. Examples are not exhaustively enumerated herein.

When the angle calculation unit is disposed, the storage unit can store a correspondence between the drive signal and the driving force of the drive unit 403, and the control unit can acquire, on the basis of the drive signal, the correspondence, and the deflection angle $\theta$, the pressure applied by the scanning assembly 108 to the tissue to be scanned. Because in this case, the correspondence between the drive signal and the pressure applied to the tissue to be scanned changes with the deflection angle $\theta$, it is difficult to directly acquire the relation between the drive signal and the pressure. In this case, the correspondence may also be obtained by performing measurement after the imaging system is installed. For example, by giving a certain current value of a drive signal, a corresponding downward pressure (in a vertically downward direction or in a downward direction along one end of the adjustable arm) of the scanning assembly 108 in this case is measured. It can be seen from the above description that the downward pressure is numerically equal to the driving force of the drive unit 403. Then, by adjusting the current value, different downward pressures described above are obtained. Then, fitting is performed on the data to obtain a correspondence between the aforementioned drive signal and the driving force of the drive unit 403. When the control unit needs to acquire the pressure applied by the scanning assembly 108 to the tissue to be scanned, the driving force can be acquired on the basis of the drive signal and the correspondence stored in the storage unit, and the pressure applied by the scanning assembly 108 to the tissue to be scanned is acquired in combination to the deflection angle $\theta$ acquired by the angle calculation unit (for example, multiplying the driving force by cos $\theta$).

The drive signal may be configured in a manner known in the art, for example, a voltage drive signal or a current drive signal is used. When a current drive signal is used, the control unit may control the magnitude of the driving force of the drive unit 403 by controlling the magnitude of the current. The greater the current, the greater the driving force correspondingly. The smaller the current, the smaller the driving force correspondingly.

As described above, the control unit can acquire the pressure applied to the tissue to be scanned. The pressure is important in a process in which the user performs imaging. The pressure affects safety of use and imaging quality. In some embodiments of the present invention, a display unit, for example, a display 110 shown in FIGS. 1 and 2, is included. The display unit is capable of displaying in real time the aforementioned pressure acquired by the control unit and applied by the scanning assembly 108 to the tissue to be scanned. The pressure displayed in real time is convenient for direct observation by the user, so that the user determines whether the pressure value is appropriate. For example, for person to be scanned having a vulnerable sternum, a low pressure is usually used. In this case, displaying the pressure value in real time presents an advantageous safety during scanning. Furthermore, an experienced user, for example, a doctor, has a certain prediction for pressure values with high imaging quality. According to prediction of the user in combination with the pressure displayed in real time, the user can select whether to increase or decrease the pressure. The pressure may be increased or decreased by increasing or decreasing the drive signal (e.g., the current) described above. It should be noted that the display unit may be the display 110 described above, and may also be another display unit disposed anywhere else. For example, additionally disposing the display unit on the scanning assembly 108 is convenient for observation by the user holding the scanning assembly 108. Alternatively, the display unit can be a mobile display terminal such as a mobile phone or a tablet computer that communicates by means of a wireless connection or the like.

In some embodiments, an input unit may further be disposed to facilitate generation of a user instruction. The user can send an instruction to the control unit by means of the input unit. The control unit may generate a corresponding drive signal in response to the instruction, and then send the drive signal to the drive unit 403.

The form of the input unit may be various. For example, the input unit may be the key shown in FIG. 3 (including the first weight adjustment button 316 and the second weight adjustment button 318). The first weight adjustment button 316 may generate an instruction to decrease the current value of the drive signal, and send the instruction to the control unit. Upon receiving the instruction, the control unit generates a drive signal with a decreased current in response to the instruction, thereby eventually achieving the effect of deceasing the pressure applied to the tissue to be scanned. Correspondingly, the second weight adjustment button 318 may generate an instruction to increase the current value of the drive signal, and send the instruction to the control unit. Upon receiving the instruction, the control unit generates a drive signal with an increased current in response to the instruction, thereby eventually achieving the effect of increasing the pressure applied to the tissue to be scanned. It should be understood that the first weight adjustment button 316 may also be used to generate an instruction to increase the current value, and correspondingly, the second weight adjustment button 318 may be used to generate an instruction to decrease the current value. The above instructions may allow the current value to be adjusted according to a preset stepped manner (for example, pressing a button once to increase or decrease the current by 0.05 A); or, non-stepped pressure adjustment may be also implemented by means of continuous current value adjustment. In addition to user input performed by means of the key, other types of input unit configurations are also allowed. For example, a user input 244 portion (e.g., a touch screen) of the display 110 is shown in FIG. 3. By means of the touch screen structure, the user can implement instruction generation by means of a certain gesture operation, for example, sliding the screen. The user may further directly input a particular instruction (e.g., a particular pressure value) to adjust the pressure. Voice input may further be used as an input unit configuration, for example, a microphone. The user vocally selects the required pressure value as an instruction to transmit the instruction to the control unit, thereby eventually implementing the pressure adjustment. The configuration of the input unit ensures that the user can control the pressure applied by the scanning assembly 108 to the tissue to be scanned.

As described above, the value of the pressure applied by the scanning assembly to the tissue to be scanned is very important to safe use by the user. An overly high pressure may cause body damage to the person to be scanned. On the basis of this, a variety of measures for ensuring a safe pressure are adopted in some embodiments of the present invention.

In some embodiments, the ultrasonic imaging system of the present invention may include an alarm unit 229. The position of the alarm unit 229 may be any position, for example, in the scanning assembly 108 shown in FIG. 2, or on the user interface 242 of the display 110. A certain safe pressure threshold value may be preset, and the threshold value may be automatically set according to information such as age and health of the subject to be scanned, or may also be manually set by the user. For example, the safe pressure threshold value for the elderly or a person with osteoporosis is set automatically or manually to a smaller value. When the pressure applied by the scanning assembly 108 to the tissue to be scanned exceeds the set threshold value, the alarm unit 229 may issue an alarm signal to inform the user. Such alarm signals may include, but are not limited to: a visual signal (e.g., providing an indication on the display 110), an audible signal (e.g., issuing a beep alert), a tactile signal (e.g., generating vibrations at a handle of the scanning assembly 108), and the like. Examples are not exhaustively enumerated herein.

In addition to the alarm unit, safety of the pressure value may also be ensured by setting an upper limit of the pressure from the scanning assembly 108 to the subject to be scanned. For example, the drive signal may be configured so that the aforementioned pressure does not exceed a certain threshold value. Determination of the threshold value may be as described above for the safe pressure threshold value. For example, the threshold is automatically set according to information such as age and health of the subject to be scanned, and may also be manually set by the user. It can be seen from the above description that the control unit may acquire, by means of the drive signal, the pressure applied by the scanning assembly 108 to the tissue to be scanned. In some embodiments, the control unit may be configured so that the drive signal is not greater than a certain value, and therefore the aforementioned pressure does not exceed a certain threshold value.

Figure 9:
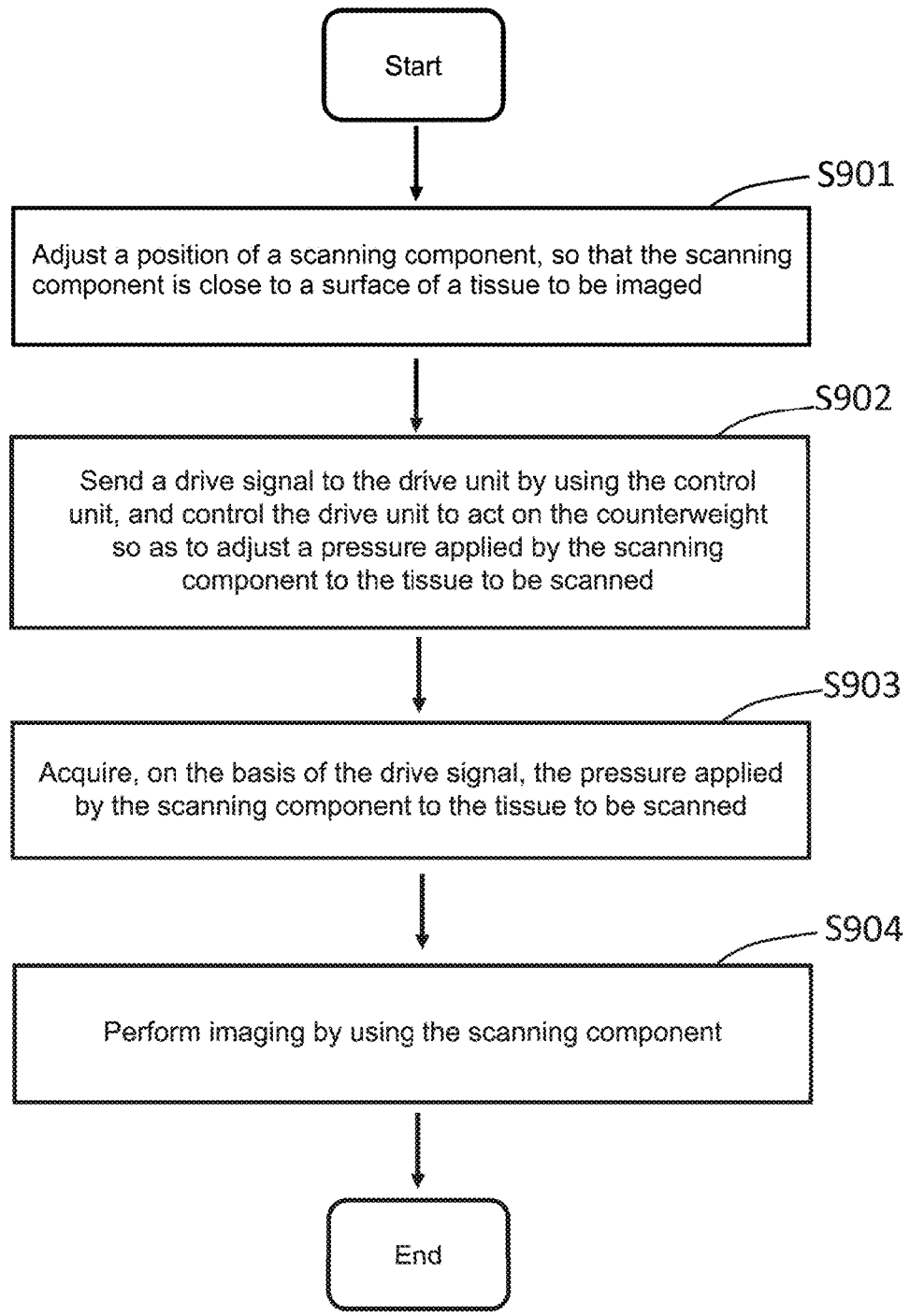
FIG. 9 is a flowchart of an ultrasonic imaging method according to an embodiment of the present invention.

As shown in FIG. 9, a flowchart of an imaging method using the imaging device of any aforementioned embodiment according to some embodiments of the present invention is shown.

In step S901, a position of the scanning assembly 108 is adjusted so that the scanning assembly is close to a surface of the tissue to be imaged. According to the above disclosure, in some embodiments, the weight of the counterweight 200 is particularly designed, and is approximately equal to the sum of the weights of the adjustable arm 106 and the scanning assembly 108. In this case, an operator can easily adjust the position of the scanning assembly 108. Since such configuration ensures that the scanning assembly 108 is substantially neutrally buoyant, only a relatively small upward or downward force is needed to be applied to the scanning assembly so as to adjust the position thereof in the vertical direction, so that the scanning assembly 108 can be close to the surface of the tissue to be imaged so as to prepare for the subsequent imaging.

Subsequently, step S902 may be performed to send a drive signal to the drive unit 403 by using the control unit, and control the drive unit 403 to act on the counterweight 401 so as to adjust a pressure applied by the scanning assembly 108 to the tissue to be scanned. The principle of the pressure adjustment is described in detail above. For example, the control unit may transmit a drive signal (e.g., a current) to the drive unit 403, and the drive unit acts on the counterweight 401 by means of the transmission unit 404, so as to adjust the pressure applied by the scanning assembly 108 to the tissue to be scanned. By adjusting the drive signal, a pressure value that is optimal for imaging and safe for the user can be determined.

In step S903, a pressure applied by the scanning assembly 108 to the tissue to be scanned is acquired on the basis of the drive signal. The step of acquiring the pressure has been described in detail above, and will not be described herein again.

In step S904, imaging may be performed by using the scanning assembly 108. The transducer array 222 in the scanning assembly 108 is used to transmit ultrasonic signals to the tissue to be scanned, and receive echo signals, and the echo signals are subjected to a series of processing so as to obtain ultrasonic images of the tissue to be scanned, which will not be described herein again.

It should be noted that the order of steps S902-S904 described above may be arbitrary. Moreover, the operator may alternately perform the aforementioned steps according to actual needs. For example, during imaging, imaging quality may change for some reasons. In this case, the operator may optionally adjust the pressure of the imaging assembly again.

In addition to the aforementioned steps, a step of displaying in real time the pressure applied by the scanning assembly 108 to the tissue to be scanned may further be included. The pressure may be displayed in real time on any display device (e.g., the display 110) as described above. The step may follow step S903 described above.

In addition, a step of inputting an instruction and sending the instruction to the control unit, so as to instruct the control unit to send the drive signal may further be included. The step may be implemented by means of an input device as described above, and will not be described herein again. The step may be configured to be prior to step S902 described above.

The method may further include: acquiring a deflection angle of the scanning assembly 108 relative to an end of the adjustable arm 106, and acquiring, on the basis of the drive signal and the deflection angle, the pressure applied by the scanning assembly 108 to the tissue to be scanned. A specific acquisition method may be as described above. For example, the deflection angle θ of the scanning assembly 108 relative to an end of the adjustable arm 106 may be calculated by using the angle calculation unit 228 in FIG. 2. On the basis of the aforementioned drive signal in combination with the deflection angle θ, the control unit 226 can acquire the pressure applied by the scanning assembly 108 to the tissue to be scanned.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

The invention claimed is:

1. An ultrasonic imaging system, comprising:
    a scanning assembly, comprising an ultrasonic transducer, and configured to perform ultrasonic imaging on a tissue to be scanned;
    an adjustable arm, a first end of the adjustable arm being connected to the scanning assembly;
    a counterweight, connected to a second end of the adjustable arm by means of a cable;
    a transmission assembly, comprising a drive unit and a transmission unit, wherein the drive unit comprises a motor and the transmission unit comprises a driving belt, the drive unit being capable of acting on the counterweight by means of the transmission unit to adjust a pressure applied by the scanning assembly to the tissue to be scanned;
    an angle calculation unit, disposed on the scanning assembly, configured to measure a deflection angle of the scanning assembly relative to the first end of the adjustable arm; and
    a control unit configured to send a drive signal to the drive unit and to acquire, on the basis of both the drive signal and the deflection angle, the pressure applied by the scanning assembly to the tissue to be scanned.

2. The ultrasonic imaging system according to claim 1, wherein the angle calculation unit comprises at least one of an accelerometer, a gyroscope, and an inertial measurement unit.

3. The ultrasonic imaging system according to claim 1, wherein the drive signal comprises at least one of a voltage drive signal or a current drive signal.

4. The ultrasonic imaging system according to claim 1, further comprising:
    a display unit capable of displaying, in real time, the pressure acquired by the control unit and the pressure applied by the scanning assembly to the tissue to be scanned.

5. The ultrasonic imaging system according to claim 1, further comprising:
    an input unit configured to send a user instruction to the control unit, wherein the input unit comprises at least one of a key, a touch screen, or a microphone; and
    wherein the control unit generates the drive signal in response to the user instruction and sends the generated drive signal to the drive unit.

6. The ultrasonic imaging system according to claim 1, further comprising:
    a storage unit configured to store a correspondence between the drive signal and the pressure applied by the scanning assembly to the tissue to be scanned; and
    wherein the control unit acquires, on the basis of the drive signal and the correspondence, the pressure applied by the scanning assembly to the tissue to be scanned.

7. The ultrasonic imaging system according to claim 1, wherein the drive unit further comprises a clutch, wherein the clutch is connected to both the motor and the transmission unit.

8. The ultrasonic imaging system according to claim 1, further comprising:
    an alarm unit configured to emit an alarm signal when the pressure exceeds a set threshold value, wherein the alarm signal is selected from the group comprising:

providing an indication on a display unit, issuing a beep alert, and generating vibrations at a handle of the scanning assembly.

9. The ultrasonic imaging system according to claim 1, wherein the drive signal is configured so that the pressure does not exceed a threshold limit.

10. A method for performing ultrasonic imaging, comprising:

adjusting a position of a scanning assembly, so that the scanning assembly is close to a surface of a tissue to be imaged;

acquiring a deflection angle of the scanning assembly relative to a first end of the adjustable arm;

sending, by a control unit, a drive signal to a drive unit, wherein the drive signal controls the drive unit to act on a counterweight to adjust a pressure applied by the scanning assembly to the tissue to be scanned;

acquiring, on the basis of both the drive signal and the deflection angle, the pressure applied by the scanning assembly to the tissue to be scanned; and performing ultrasonic imaging by using the scanning assembly.

11. The method according to claim 10, further comprising:

displaying, in real time, the pressure applied by the scanning assembly to the tissue to be scanned.

12. The method according to claim 10, further comprising:

inputting a user instruction; and sending the user instruction to the control unit to instruct the control unit to send the drive signal.

\* \* \* \* \*